United States Patent [19]
Schuetz

[11] Patent Number: 5,129,821
[45] Date of Patent: Jul. 14, 1992

[54] ORTHODONTIC BRACKET FOR CORRECTING MALALIGNED TEETH

[76] Inventor: Winfried Schuetz, Wilhelm-Högner-Str. 58, D-8000 Munchen 83, Fed. Rep. of Germany

[21] Appl. No.: 657,239

[22] Filed: Feb. 20, 1991

[30] Foreign Application Priority Data

Feb. 21, 1990 [DE] Fed. Rep. of Germany ....... 4005387

[51] Int. Cl.⁵ ................................................. A61C 3/00
[52] U.S. Cl. ........................................... 433/8; 433/10
[58] Field of Search ................................. 433/8, 9, 10

[56] References Cited

U.S. PATENT DOCUMENTS

| | | | |
|---|---|---|---|
| 4,545,760 | 10/1985 | Förster | 433/9 |
| 4,614,497 | 9/1986 | Kurz | 433/8 |
| 4,634,662 | 1/1987 | Rosenberg | 433/10 |
| 4,838,786 | 6/1989 | Reher et al. | 433/9 |
| 4,927,360 | 5/1990 | Pospisil | 433/8 |

Primary Examiner—Gene Mancene
Assistant Examiner—Cindy A. Cherichetti
Attorney, Agent, or Firm—Laurence R. Brown

[57] ABSTRACT

The invention relates to a bracket (1, 21) for an arch wire (6) for correcting malaligned teeth having a saucer-shaped base (2, 22) to be provided on a tooth, a bracket foot (3, 23) seated on the base, and a slot (5, 25) on the upper side of the bracket foot for integrating the arch wire (6). To obtain a small bracket and reduce the danger of the bracket being bitten off, in particular when the brackets are used for teeth in the lower jaw, the invention proposes providing one side wall (4, 24) of the bracket (1, 21), namely the side wall facing the masticatory surface, with a flat outside wall (4, 24) without protruding elements, at least in the area of the slot (5, 25). An apparatus for taking up an attachment aid can be formed in this outside wall, e.g. in the form of a lug (13) or a groove or channel (16) open toward the bracket foot.

7 Claims, 3 Drawing Sheets

ORTHODONTIC BRACKET FOR CORRECTING MALALIGNED TEETH

The present invention relates to a bracket or holding clamp.

To correct malaligned teeth one uses a fixed appliance, a so-called multiband or multibracket appliance. One cements to the surface of the teeth brackets having a base conforming with the tooth surface and cemented thereto and a bracket foot having a slot of rectangular cross section formed on its upper surface. The slots of the brackets take up an arch wire of circular or likewise rectangular cross section that extends in a plane following the shape of a normal jaw. The arch wire is held in position in the slots of the brackets by an attachment aid, e.g. a ligature wire or a rubber ring. The brackets have different shapes for different teeth, in particular with respect to the height of the bracket foot and the inclination of the slot in this bracket foot, these dimensions being selected in such a way that if the teeth were correctly aligned the straight arch wire would fit the slots and could be placed therein without resistance. The brackets are positioned on the tooth surfaces with respect to the angular position relative to the desired straight course of the jaw and the arch wire in such a way that the arch wire is deformed upon insertion in the slots but, due to its elasticity, exerts forces on the brackets and thus on the teeth so that at the end of treatment, when the teeth are correctly aligned, the arch wire is "straight".

In the lower jaw the brackets are frequently "bitten off" despite their smallness, in particular if a strong overbite exists, since the teeth of the upper jaw, during chewing, constantly hit wings on the top of the bracket that are required for taking up an attachment aid, e.g. a ligature or the like.

The invention is based on the problem of stating a simple construction for a bracket that requires little space, whereby the bracket can also be used in particular if an extreme overbite exists.

A further object of the invention is to state a bracket wherein the arch wire can be held reliably with an attachment aid, e.g. a ligature wire, whereby the ligature wire does not extend substantially beyond the contour of the bracket, in particular on the side wall facing the masticatory surface.

A further object is to design the side wall of the bracket facing the masticatory surface in such a way as to permit easy application of an attachment aid, e.g. a ligature wire, for holding the arch wire in the bracket slot.

A further object of the invention is to make the side of the bracket facing the masticatory surface as small as possible without providing disturbing projections such as holding clamps or the like for a ligature wire, while maintaining the stability of the bracket under the forces of the arch wire.

Accordingly, one side wall of the bracket is of flat design or lies in a plane at least in the area of the slot, but preferably in the total area. It serves in the area of the slot only as its limiting wall and is preferably only thick enough there to take up the twisting forces of the arch wire.

Such an embodiment is of smaller construction than known bracket forms since the wings for taking up the attachment aid can be omitted at least on one side of the bracket. If the brackets are used for the teeth of the lower jaw and this flat side wall faces the masticatory surface, there is a substantially smaller danger of the brackets being bitten off. It is therefore often no longer necessary in the case of an overbite to correct the position of the teeth in the upper jaw before providing brackets in the lower jaw, so that the latter can be placed earlier and the duration of treatment altogether shortened.

The inventive design of the brackets furthermore has the advantage that the surface form of the bracket is simpler, so that fewer food particles cling to the appliance and the latter is easier to clean.

The attachment aid, e.g. a ligature wire or rubber ring, is taken up according to a preferred embodiment of the invention by a lug open toward the base and disposed in the immediate vicinity of the base approximately in the middle of the bracket foot. A ligature wire can be threaded in this lug from below, whereby this threading can be facilitated by inwardly indenting the wall of the bracket in the area of the lug in the manner of a groove. On the opposite side of the bracket foot its side wall has, in the conventional way, either two wings or another suitable means for taking up the ligature wire or rubber ring.

A power arm can additionally be provided on this side wall. Such a power arm with a holding bar extending perpendicular to the slot serves, for instance, to connect brackets on successive teeth with rubber rings so as to exert a force between the brackets and thus between the teeth that is also used to correct the position of the teeth.

Instead of providing a lug in the lower area of the limiting wall one can also place a groove or channel here that opens toward the bracket foot. This facilitates the application of a ligature wire. The side wall limiting the bracket slot need not extend over the entire length of the bracket slot. It is sufficient for the side wall to extend to the left and right of the center over such a length that the bracket slot extends beyond both edges to the left and right of the side wall. This side wall has a lug open toward the base of the bracket or a channel or groove extending over the entire width of this side wall. This design simplifies the application of a ligature wire even further without impairing the stability of the bracket.

Further embodiments of the invention can be found in the subclaims. The invention shall be explained in more detail in exemplary embodiments with reference to the drawing, in which FIGS. 1 and 2 show perspective views of a bracket according to the invention;

Figure 1:
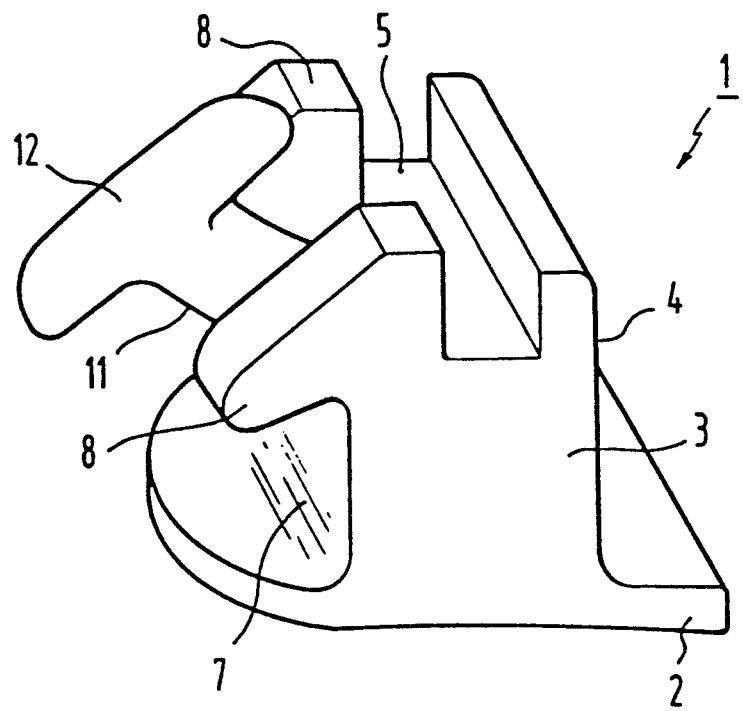
Figure 2:
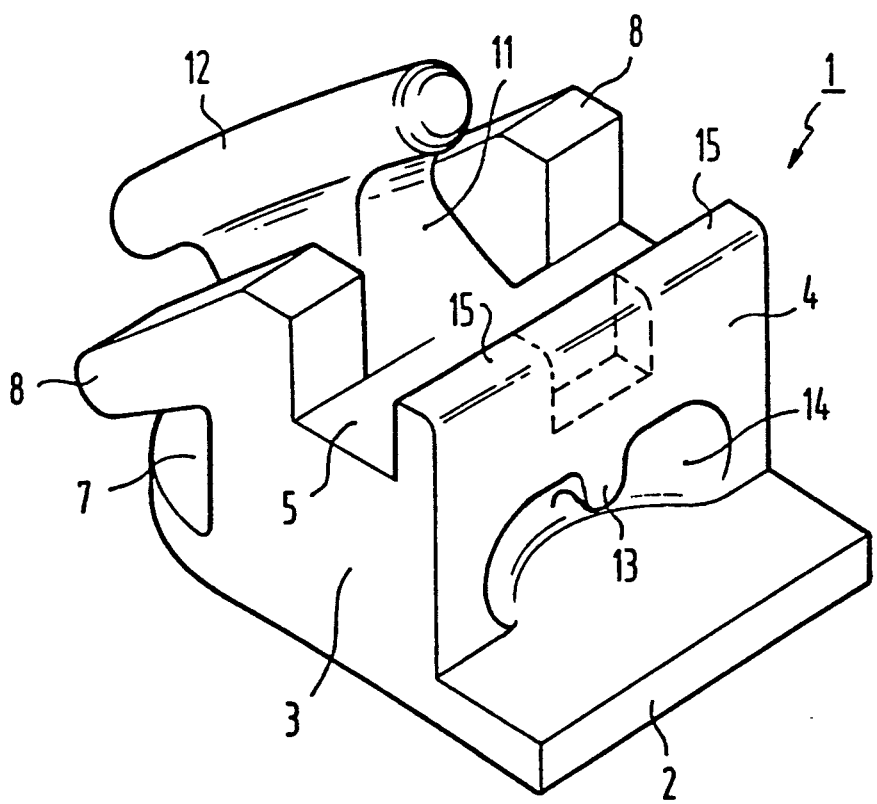
Figure 3:
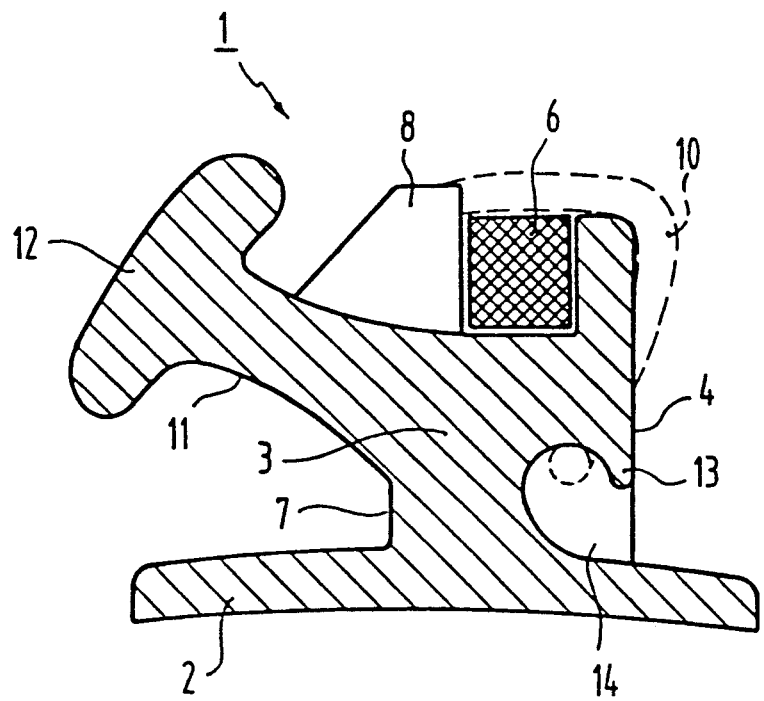
FIG. 3 shows a central cross section through the bracket according to FIGS. 1 and 2.

FIGS. 1 to 3 show a bracket 1 with a base 2 and a bracket foot 3 of approximately rectangular cross section disposed thereon. One side wall 4 of the bracket is flat and the limiting wall for a slot 5 of rectangular cross section on the upper side of the bracket foot, into which an arch wire 6 is inserted; cf. FIG. 3. In the case of a steel bracket the limiting wall 4 has a thickness of about 0.3 to 0.5 mm. In particular if the bracket is used in the lower jaw this side wall 4 faces the masticatory surface.

Both edges of opposite side wall 7 of the bracket are provided with hook-shaped claws 8 that limit the slot and under whose outwardly pointing hooks a ligature wire 10, for example, shown by broken lines in FIG. 3 for fixing the arch wire can be looped. A power arm 11 with a holding bar 12 perpendicular to the slot 5 is disposed on this side wall 7 of the bracket.

On flat limiting wall 4 a lug 13 open toward base 2 is situated in the area of the later, about which said ligature wire 10 can be threaded. Flat side wall 4 has in the area of lug 13 an inward groove or indentation 14 so that the ligature wire can be threaded more easily into the lug from both sides of it.

As apparent from FIG. 3, the lug does not protrude out of the plane of limiting wall 4. This would be possible, but in case of an overbite it should not protrude so far that the patient's teeth touch the hook of the lug. What is essential is that limiting wall 4 has no outwardly protruding parts at least in the area of slot 5.

Flat limiting wall 4 along the slot can be interrupted so that only two pillars 15 remain opposite claws 8, as suggested in FIG. 2 by broken lines.

Figure 4:
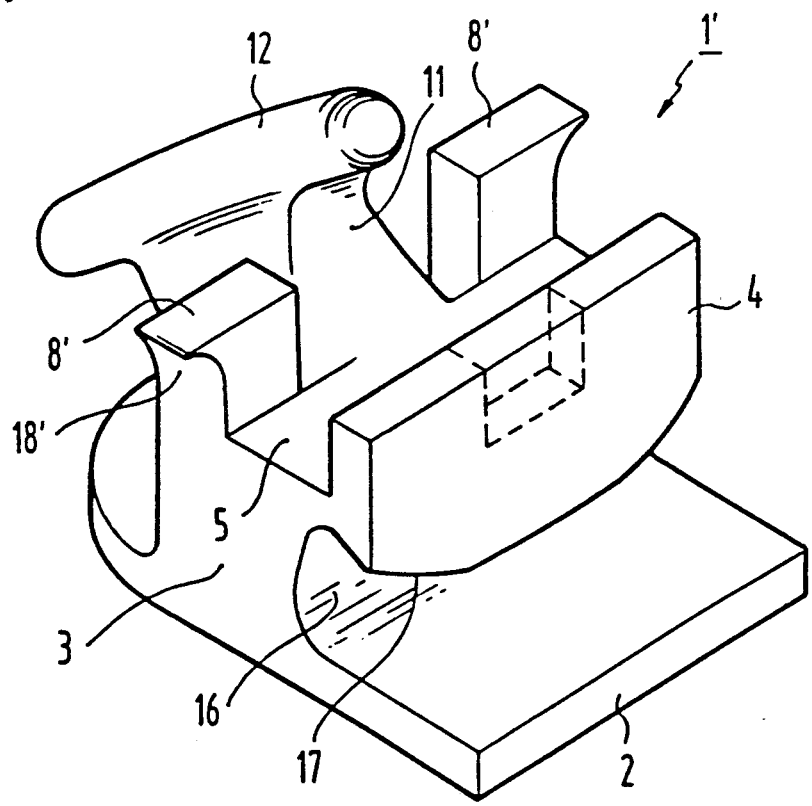
FIG. 4 shows a perspective view of a modified embodiment of a bracket.

FIG. 4 shows a bracket 1' that is slightly modified over that in FIGS. 1 to 3, so that the same reference numbers are used for the same parts. Instead of the lug therein, a channel-like groove 16 is provided for holding a ligature, that extends over the entire width of the bracket and from flat side wall 4 into bracket foot 3. The upper lateral edges of this channel can slope upwardly in the direction of the slot, as suggested by 17. Instead of the hook-shaped claws in the above embodiment example, only pillars 8' are used here, their outer walls 18 protruding outwardly so that a ligature wire placed around them cannot slip off upwardly.

Figure 5:
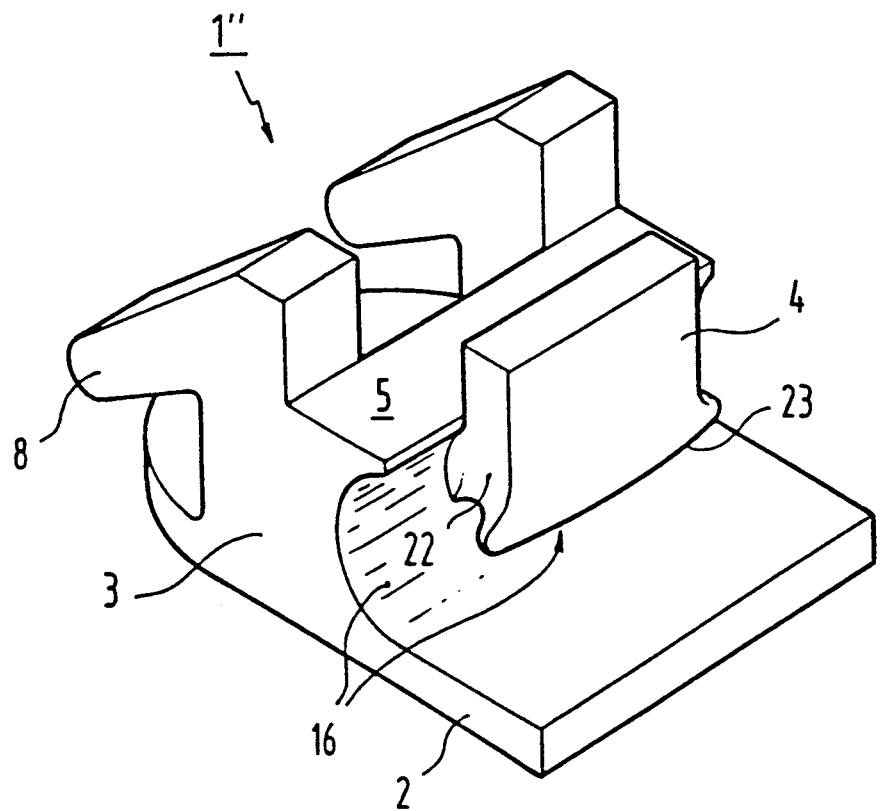
FIG. 5 shows a bracket according to a third embodiment.
Figure 6:
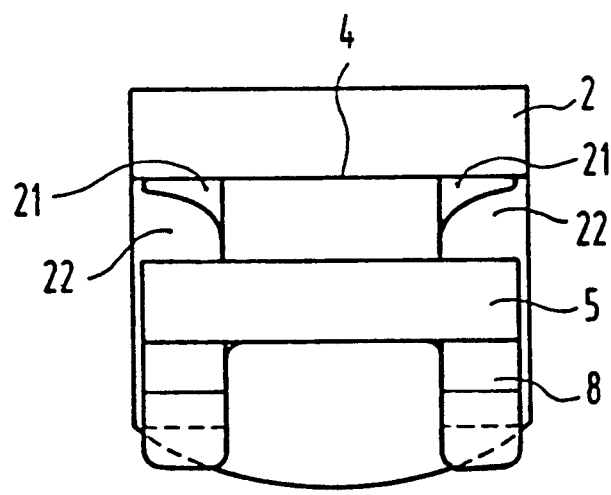
FIG. 6 shows a top view of the bracket according to FIG. 5.

FIGS. 5 and 6 show a further embodiment of a bracket 1" that is substantially derived from the construction of a bracket according to FIG. 4 as far as the flat side wall is concerned. Bracket 1" has a base 2, a bracket foot 3, a bracket slot 5, two claws 8 on the side of the bracket facing the gum, and a side wall 4 extending only over part of the length of bracket slot 5 so that the latter extends beyond the two edges of this side wall 4. Between base 2 and side wall 4 there is a groove or channel 16 in which a ligature wire can be inserted, as described above. To ensure a reliable hold for the ligature wire and also to facilitate its insertion, the outer edges of side wall 4 are drawn toward the front and rear sides of the bracket, as shown in FIG. 6, so as to form quasi claws 21 there. These claws 21 and the side wall of the bracket in the area of bracket foot 3 limit a groove 22 in which a ligature wire is guided well. Groove or channel 16 extending along the lower edge of side wall 4 has a slight curve, as suggested in FIG. 5 by 23, so that a ligature wire can be inserted in this groove with minimal bends and then guided over the arch wire and placed about claws 8.

This construction gives the bracket high stability while permitting it to be very small. It also simplifies the application of a ligature.

I claim:

1. A bracket for an arch wire for correcting maligned teeth having a saucer or plate-shaped base to be provided on a tooth, a bracket foot seated on the base, and a bracket slot (5) on the upper side of the bracket foot for taking up or integrating the arch wire, characterized in that one side wall (4) of the bracket (1) is only a limiting wall alongside the slot (5) and has an outer surface lying substantially in a plane substantially perpendicular to the base at least in the area of this slot, wherein the side wall (4) is located on the side of the masticatory surface of the teeth and has in an outer surface a recess provided in the bracket near the base of the bracket to extend substantially underneath said slot (5), said side wall and recess forming holding means (13) about which an attachment aid, e.g. a ligature wire (10), may be threaded in a position in the area of the base (2) of the bracket (1) the holding means being adapted to surround the attachment aid partially on an upper side away from the base thereby to hold the attachment aid in a position near to the base.

2. The bracket of claim 1, characterized in that the means about which the attachment aid (10) may be threaded is a lug (13) open toward the base (2) and disposed approximately in the center of the bracket foot (3).

3. The bracket of claim 2, characterized in that said recess (14) is provided in the side wall (4) below the lug (13).

4. The bracket of claim 1, characterized in that the holding means about which the attachment aid may be threaded is a channel (16) open toward the base (2).

5. The bracket of claim 4, characterized in that lateral ends (17) of the channel (16) are slanted upwardly toward the bracket slot (5).

6. The bracket of claim 4, characterized in that the channel (16) extends over the entire width of the bracket foot (3) and constitutes said recess.

7. The bracket of claim 4, characterized in that the side wall (4) of the bracket extends with its outside wall lying substantially in a plane over only part of the length of the bracket slot (5).

* * * * *